(12) United States Patent
van Hal et al.

(10) Patent No.: US 10,106,474 B2
(45) Date of Patent: *Oct. 23, 2018

(54) PROCESS FOR PRODUCING PROPYLENE AND AROMATICS FROM BUTENES BY METATHESIS AND AROMATIZATION

(71) Applicant: SAUDI BASIC INDUSTRIES CORPORATION, Riyadh (SA)

(72) Inventors: Jaap W. van Hal, Fresno, TX (US); Scott A. Stevenson, Houston, TX (US); Jim Allman, Sugar Land, TX (US); David L. Sullivan, Sugar Land, TX (US); Travis Conant, Sugar Land, TX (US)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 734 days.

This patent is subject to a terminal disclaimer.

(21) Appl. No.: 14/171,905

(22) Filed: Feb. 4, 2014

(65) Prior Publication Data

US 2014/0148629 A1    May 29, 2014

Related U.S. Application Data

(63) Continuation of application No. 12/767,080, filed on Apr. 26, 2010, now Pat. No. 8,722,950.

(51) Int. Cl.
*C07C 2/76* (2006.01)
*C07C 6/04* (2006.01)
*C07C 5/41* (2006.01)

(52) U.S. Cl.
CPC ............... *C07C 2/76* (2013.01); *C07C 5/417* (2013.01); *C07C 6/04* (2013.01); *C07C 2521/04* (2013.01);

(Continued)

(58) Field of Classification Search
USPC ................ 585/322, 324, 407, 643, 646, 647
See application file for complete search history.

(56) References Cited

U.S. PATENT DOCUMENTS

| 4,151,071 A | 4/1979 | Myers |
| 4,609,769 A | 9/1986 | Kukes et al. |

(Continued)

FOREIGN PATENT DOCUMENTS

WO      03076371 A1    9/2003

OTHER PUBLICATIONS

International Search Report; International Application No. PCT/US2001/033059: International Filing Date: Apr. 19, 2011; dated Jun. 22, 2011; 4 Pages.

(Continued)

*Primary Examiner* — Thuan D Dang
(74) *Attorney, Agent, or Firm* — Cantor Colburn LLP (57) ABSTRACT

The disclosure is for a process for producing propylene and hexene (along with ethylene, pentenes, product butenes, heptenes and octenes) by metathesis from butenes (iso-, 1- and cis and trans 2-) and pentenes and then aromatizing the hexenes (along with higher olefins, such as heptenes and octenes) to benzene (along with toluene, xylenes, ethylbenzene and styrene). Since the desired products of the metathesis reaction are propylene and hexene, the feed to the metathesis reaction has a molar ratio for 1-butene:2-butene which favors production of propylene and 3-hexene with the concentration of hexenes and higher olefins in the metathesis product being up to 30 mole %. An isomerization reactor may be used to obtain the desired molar ratio of 1-butene:2-butene for the feed composition into the metathesis reactor. After the metathesis reaction, of hexene and higher olefins are separated for aromatization to benzene and other aromatics.

17 Claims, 5 Drawing Sheets

(52) U.S. Cl.
CPC ...... *C07C 2521/08* (2013.01); *C07C 2523/28* (2013.01); *C07C 2523/30* (2013.01); *C07C 2523/36* (2013.01); *C07C 2529/54* (2013.01); *C07C 2529/62* (2013.01)

(56) References Cited

U.S. PATENT DOCUMENTS

| | | |
|---|---|---|
| 5,091,351 A | 2/1992 | Murakawa et al. |
| 6,420,619 B1 | 7/2002 | Gartside et al. |
| 6,538,168 B1 | 3/2003 | Schwab et al. |
| 6,580,009 B2 | 6/2003 | Schwab et al. |
| 6,646,172 B1 | 11/2003 | Schwab et al. |
| 6,683,019 B2 | 1/2004 | Gartside et al. |
| 6,777,582 B2 | 8/2004 | Gartside et al. |
| 7,214,841 B2 | 5/2007 | Gartside et al. |
| 7,223,895 B2 | 5/2007 | Sumner et al. |
| 7,576,251 B2 | 8/2009 | Gartside et al. |
| 7,608,745 B2 | 10/2009 | Hildreth et al. |
| 8,299,313 B2 | 10/2012 | Takai et al. |
| 2006/0047176 A1 | 3/2006 | Gartside et al. |
| 2006/0235252 A1 | 10/2006 | Gartside et al. |
| 2006/0235254 A1 | 10/2006 | Gartside et al. |
| 2006/0235255 A1 | 10/2006 | Gartside et al. |
| 2008/0255398 A1 | 10/2008 | Stevenson et al. |
| 2010/0041930 A1 | 2/2010 | Gartside et al. |
| 2010/0056839 A1 | 3/2010 | Ramachandran et al. |

OTHER PUBLICATIONS

Written Opinion of the International Searching Authority; International Application No. PCT/US2001/033059; International Filing Date: Apr. 19, 2011; dated Jun. 22, 2011; 7 Pages.

Studies in Surface Science and Catalysis; 2001; 135; p. 278; (3 pages).

Figure 3: Calculated and observed product distribution for 75 % 1-butene in feed for Re catalysts at 48 °C

PROCESS FOR PRODUCING PROPYLENE AND AROMATICS FROM BUTENES BY METATHESIS AND AROMATIZATION

CROSS-REFERENCE TO RELATED APPLICATION

This application is a Continuation of U.S. Non-Provisional Patent Application Ser. No. 12/767,080 filed Apr. 26, 2010. The related application is incorporated herein by reference.

TECHNICAL FIELD

This disclosure relates to a process for producing propylene, hexenes and, optionally, ethylene, by metathesis from butenes and pentenes and then aromatizing the hexenes to benzene.

BACKGROUND

Olefin metathesis is the catalytic double disproportionation by cleavage and reformation of the carbon double bond (C=C) of two olefin compounds to form two different olefin compounds. This reaction is reversible, and the overall product distribution is limited by a thermodynamic equilibrium. The catalysts are generally homogeneous or heterogeneous transition metal compounds, particularly compounds of transition metal Groups VI to VIII.

U.S. Pat. No. 6,646,172 discloses a multistage process for preparing propylene from metathesis of butenes and from separate metathesis of the $C_5$ alkenes produced in the metathesis of butenes.

U.S. Pat. No. 6,580,009 discloses a process for preparing propylene and hexene by metathesis of a raffinate II feedstream of olefinic $C_4$ hydrocarbons and ethene with fractional distillation to recover butanes, butenes and a pentene-containing fraction for recycle. This patent also discloses methods for the removal of butadiene, acetylenic compounds, and oxygen-containing impurities from a $C_4$ feedstream.

U.S. Pat. No. 6,538,168 discloses a process for preparing $C_5$-$C_6$ olefins by metathesizing butenes into a mixture of $C_2$-$C_6$ olefins and butanes, separating $C_2$-$C_3$ olefins from $C_4$-$C_6$ olefins, further separating $C_4$-$C_6$ olefins into hexene and methylpentene and a recycle of butanes, butenes, pentene and methylbutene.

U.S. Pat. No. 6,777,582 discloses a process for metathesis of 1-butene and 2-butene to propylene and 2-pentene which is recycled with product butenes to form propylene and hexene.

Aromatization of alkenes is a process of dehydrogenation, cyclization and aromatization of the alkene. The catalyst for this process must be multi-functional to have an acceptable conversion and selectivity for the desired products. Aluminosilicate zeolites are known catalysts for aromatization. Some zeolite catalysts for aromatization contain a Group VIII deposited metal, such as platinum, and elements other than silicon and aluminum, such as germanium, in the zeolite crystalline framework.

U.S. Patent Application Publication no. 2008/0255398 discloses a process for the aromatization of $C_6$ to $C_{12}$ alkanes, such as hexane, heptane and octane, to aromatics, such as benzene, ethyl benzene, toluene and xylenes, with a non-acidic aluminum-silicon-germanium MFI zeolite on which platinum has been deposited. One catalyst for the aromatization of $C_6$ to $C_{12}$ alkanes is Pt/CsGeZSM-5.

Metathesis of butenes is known in the prior art. It is known that metathesis of 1-butene, 2-butene and isobutene will yield propylene, a desirable product which can be further processed into other compounds, such as acrylic acid, acrylonitrile, isopropanol, propylene oxide, and into other products, such as polypropylene. Commercialization of metathesis of butenes has been impeded due to the lack of uses for the other products of the metathesis reaction, such as hexene and higher olefins. Since metathesis is an equilibrium reaction, these products which have been less desirable than propylene are produced in an amount beyond what is useful for their available market. It would be advantageous to convert these products to more marketable products.

SUMMARY

The present disclosure is for a multi-step process which produces propylene and hexene (along with ethylene, pentenes, product butenes, heptenes and octenes) from butenes (1-, cis and trans 2- and iso-) by metathesis followed by aromatization of the hexene (along with higher olefins, such as heptenes and octenes) to benzene (along with toluene, xylenes, ethylbenzene and styrene). Pentenes and butenes from the metathesis step are recycled. Ethylene may also be recycled or separated for further processing. Propylene is separated for further processing. Any metathesis catalyst could be used for metathesizing butenes. Any aromatization catalyst could be used for aromatizing hexene and higher olefins.

BRIEF DESCRIPTION OF THE DRAWINGS

A more complete appreciation of the disclosure and many of the attendant advantages thereof will be readily understood by reference to the following detailed description when considered in connection with the accompanying drawings.

DETAILED DESCRIPTION

The process of the present disclosure produces propylene and aromatics from feedstreams containing butenes, especially those containing 1-butene and 2-butene. The feedstreams may also contain pentenes. One example of feedstock is what is known as "raffinate II" obtained from the processing of crude $C_4$ cuts by removing butadiene from the crude $C_4$ cuts in a first step ("raffinate I") and removing isobutene from the $C_4$ stream in a second step. Raffinate II consists of mainly 1-butene and a mixture of cis and trans 2-butene. Other examples of feedstreams include cracker byproduct streams, which would contain a mixture of $C_4$ and possibly $C_5$ olefins; and streams obtained from dehydrogenation of butane and isobutane, which would contain 1-butene, 2-butene, and isobutene.

The present disclosure is for a process for producing propylene and aromatics comprising: a) reacting a hydrocarbon feed mixture comprising 1-butene, 2-butene and, optionally, isobutene in the presence of a metathesis catalyst at conditions to produce ethylene, propylene, product butenes, pentenes, hexenes and higher olefins; b1) separating and recycling the pentenes, butenes, and optionally, the ethylene from the product; b2) separating propylene from the product; b3) separating hexenes and higher olefins from the product; and c) reacting hexenes and higher olefins in the presence of an aromatization catalyst.

A metathesis catalyst can be used to convert a feed containing butenes, and possibly pentenes, into a mixture of ethylene, propylene, butenes (product and unreacted), pentenes (product and unreacted), hexenes and higher olefins. The pentenes, the butenes, and possibly the ethylene are separated and recycled to the reactor for further conversion. The propylene is separated for further processing. The hexene and higher olefins are separated for aromatization.

Any metathesis catalysts could be used in the present disclosure. Known metathesis catalysts include supported transition metal compounds of tungsten, molybdenum or rhenium, such as $WO_3$ on $SiO_2$, $MoO_3$ on $Al_2O_3$, or $Re_2O_7$ on $Al_2O_3$, and molecular catalysts such as Grubbs' or Schrock's catalysts. Metathesis catalysts may include promoters, such as compounds of transition metals, e.g., cobalt, or of alkali metals, e.g., potassium or cesium. One example of a metathesis catalyst with a promoter is $CoO/MoO_3$ on $Al_2O_3$.

If butenes and pentenes are present in the feedstream and/or recycle, there are several possible metathesis reactions. Some possibilities are given below:

In one embodiment of the present disclosure, the feed to the metathesis reaction zone would have a molar ratio for 1-butene:2-butene in the range of from about 1:6 to about 6:1. In another embodiment of the present disclosure, the molar ratio would be about 1:1 to about 3:1. In another embodiment of the present disclosure, the molar ratio would be about 2:1. With such molar ratios the likelihood of the following reactions are enhanced:

These equilibrium reactions favor the production of propylene and 3-hexene. In one embodiment of the disclosure the concentration of hexenes and higher olefins in the metathesis product is up to 30 mole %. In another embodiment of the disclosure the concentration of hexenes in the metathesis product is about three to about twenty mole %. In another embodiment of the disclosure the propylene:hexenes molar ratio is in the range of from about 1:1 to about 3:1. In another embodiment of the disclosure the propylene:hexenes molar ratio is about 2:1.

Depending on the relative amounts of the olefins in the feed and the recycle stream, an olefin isomerization reactor can balance the amounts of olefins in the feed to the metathesis reactor to a molar ratio for 1-butene:2-butene in the range of from about 1:6 to about 6:1. Any olefin isomerization catalyst could be used, including basic metal oxides (i.e. magnesium oxide, calcium oxide, barium oxide, etc.).

The metathesis reaction may be in liquid phase or gas phase. The metathesis reaction may be carried out at a temperature in the range of from about 25° C. to about 400° C. and a pressure in the range of from about 0 psig to about 500 psig. Using catalysts at low temperature could suppress the isomerization of the olefins and increase the selectivity to $C_2$-$C_6$ olefins because fewer $C_{7+}$ compounds are formed.

Since metathesis catalysts are susceptible to poisoning by a number of impurities which may be present in the feed (e.g., dienes, acetylenic compounds, polar molecules, oxygenates, sulfur compounds, and nitrogen compounds), the feed may be purified prior to its introduction to the reactor. Guard beds may be placed upstream of the catalyst bed in order to ensure removal of trace component poisons (e.g. water, oxygenates, sulfur compounds, and nitrogen compounds). U.S. Pat. No. 7,214,841 discloses that metathesis catalysts are tolerant of butadiene levels up to 10,000 ppm. In one embodiment of the present disclosure the level of all such non-diene impurities, contaminants and poisons (acetylenic compounds; polar molecules, such as water; oxygenates; sulfur compounds; nitrogen compounds and combinations thereof) in the feed is no more than 100 ppm.

After the metathesis reaction, the products are separated into at least three streams: a recycle stream of pentenes, butenes, and possibly ethylene, a product stream of propylene and a stream of hexene and higher olefins for aromatization. Separation can be by any known method in the art, e.g., reactive distillation, preferential boiling of the ethylene and propylene, or a selective membrane.

The hexenes and higher olefins are aromatized to benzene and other aromatics. Any catalyst suitable for the conversion of linear hexenes or hexanes (if the hexenes are hydrogenated) could be used for the aromatization step. Examples include zeolite catalysts, such as Pt/KL-zeolite, Pt/CsGeZSM-5, Pt/KGeZSM-5 and Pt/KZSM-5.

The contact between the hexenes and higher olefins and the catalyst may be at a liquid hourly space velocity in the range between 0.1 and 100 h$^{-1}$, at a temperature in the range between 200 and 600° C. and at a pressure in the range between 1 and 315 psia.

The disclosure having been generally described, the following examples are given as particular embodiments of the disclosure and to demonstrate the practice and advantages thereof. It is understood that the examples are given by way of illustration and are not intended to limit the specification or the claims to follow in any manner.

Metathesis Catalysts

1. $Re_2O_7$ (10 wt % Re-metal) on γ-alumina synthesized based on methods described in U.S. Pat. No. 6,130,181.

2. 4 wt % CoO, 14 wt % MoO$_3$ on alumina commercially available from Strem Chemicals.

3. 6 wt % WO$_3$ on silica synthesized based on methods described in U.S. Pat. No. 4,609,769.

EXAMPLES

All runs were performed by passing a mixture of 1-butene and 2-butene through a vertical tubular reactor (½ inch in diameter and 18 inch in length) positioned in a temperature controlled heating mantle. In each run the reactor contained a 5 g bed of the designated catalyst. The reactor pressure was held at 40 psig, and the feed flows were set to give a WHSV of 1 hr$^{-1}$.

The calculated product distributions were made with the r$_{equil}$ module of Aspen Plus, version 7, software.

Example 1: Re Catalyst at 48° C., 25% 1-Butene

Figure 2:
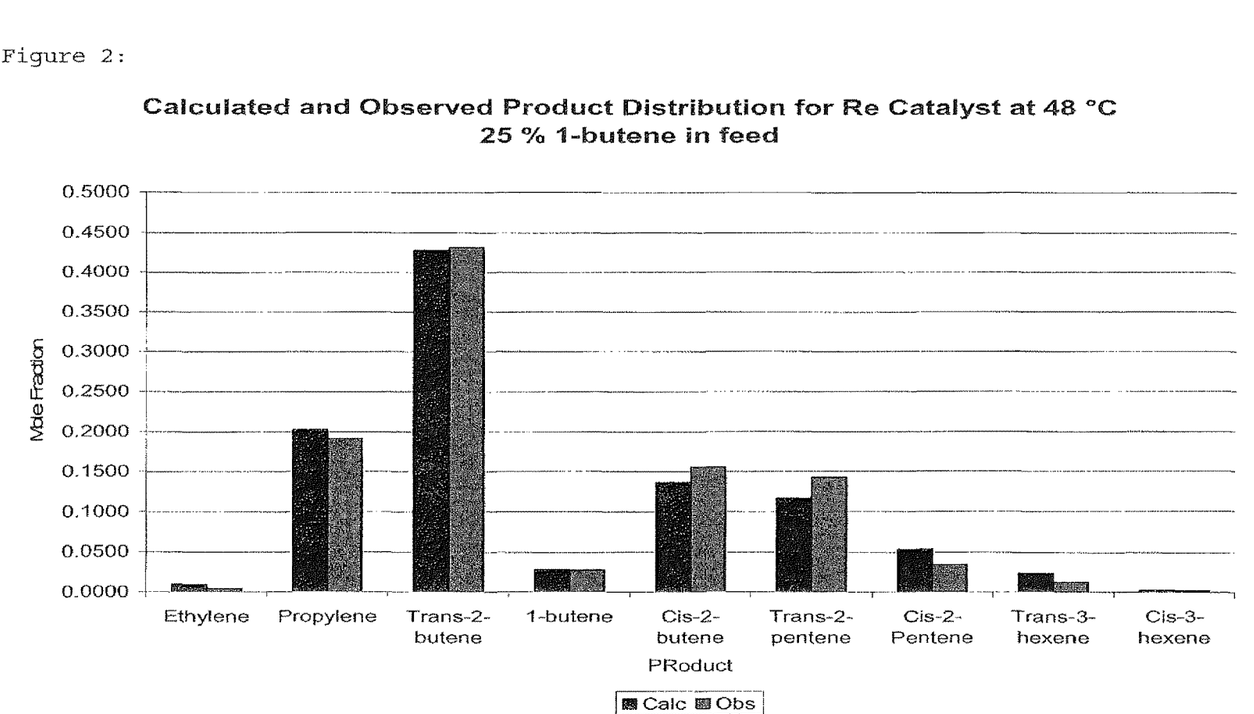
FIG. 2 is a graph comparing the calculated equilibrium and observed product distributions for metathesis of butenes with a rhenium catalyst at 48° C. and 25% 1-butene in feed (Example 1).

The feed with a 1-butene/2-butene molar ratio of 1:3 was passed continuously through a catalyst bed of Re$_2$O$_7$ on alumina (10 wt Re-metal) which was maintained at 48° C. The catalyst was previously activated in air at 500° C. Reaction product analysis after 24 hours time on stream revealed a total butenes conversion of 43% with an equilibrium distribution of products. The selectivity towards propylene was found to be 49% while the selectivity towards hexenes was 4%. The ratio of cis-3-hexene to trans-3-hexene was found to be 1:6. A comparison between the calculated equilibrium product distribution and the observed values is shown in FIG. 2.

Example 2: Re Catalyst at 48° C., 75% 1-Butene

Figure 3:
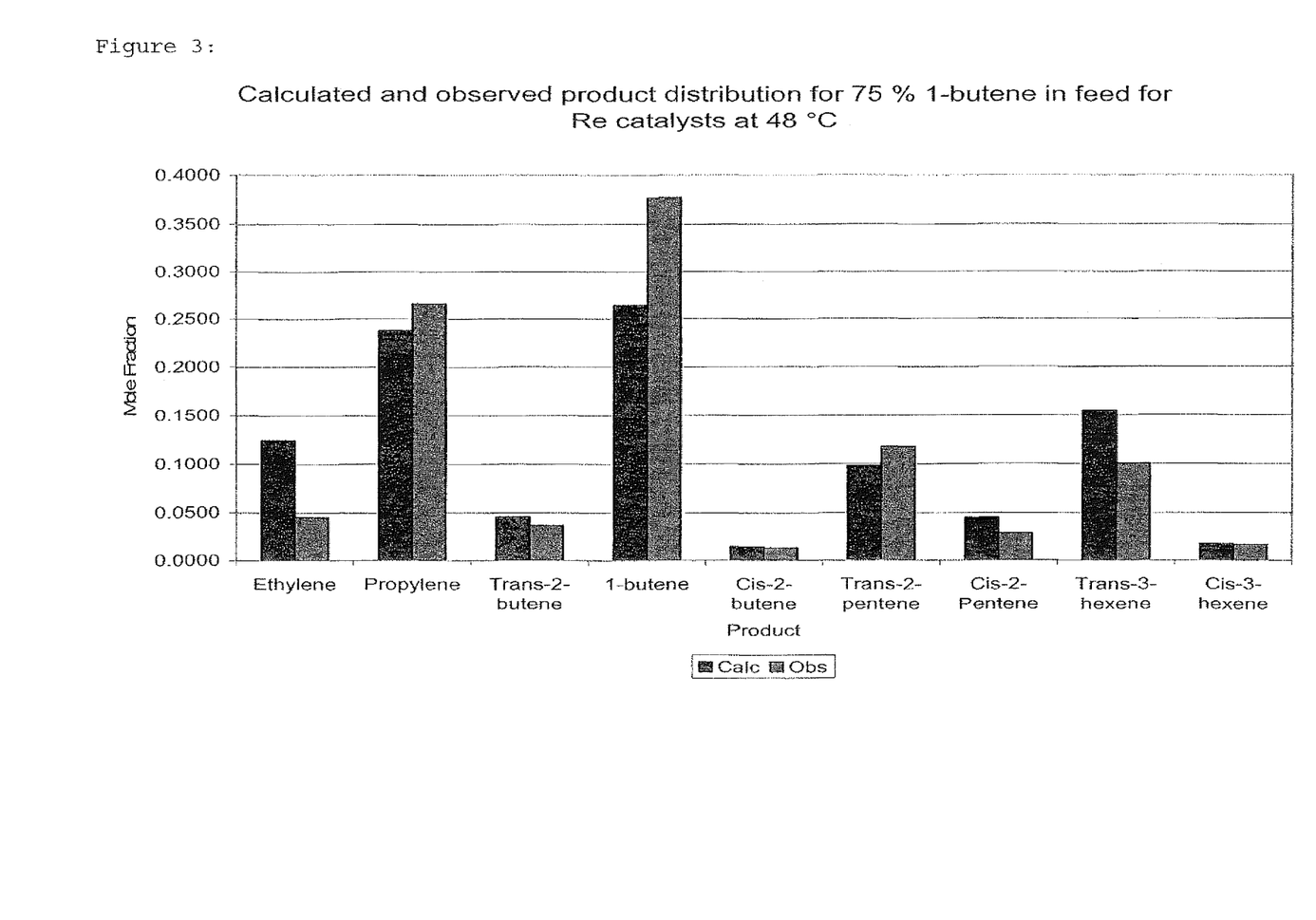
FIG. 3 is a graph comparing the calculated equilibrium and observed product distributions for metathesis of butenes with a rhenium catalyst at 48° C. and 75% 1-butene in feed (Example 2).

The feed with a 1-butene/2-butene molar ratio of 3:1 was passed continuously through the catalyst bed of Re$_2$O$_7$ on alumina (10 wt % Re-metal) which was maintained at 48° C. The catalyst was previously activated in air at 500° C. Reaction product analysis after 19 hours time on stream revealed a total butenes conversion of 59% with an equilibrium distribution of products. The selectivity towards propylene was found to be 46% while the selectivity towards hexenes was 20%. Again, the ratio of cis-3-hexene to trans-3-hexene was found to be 1:6. A comparison between the calculated equilibrium product distribution and the observed values is shown in FIG. 3.

Example 3: Co/Mo Catalyst at 97° C., 50% 1-Butene

Figure 4:
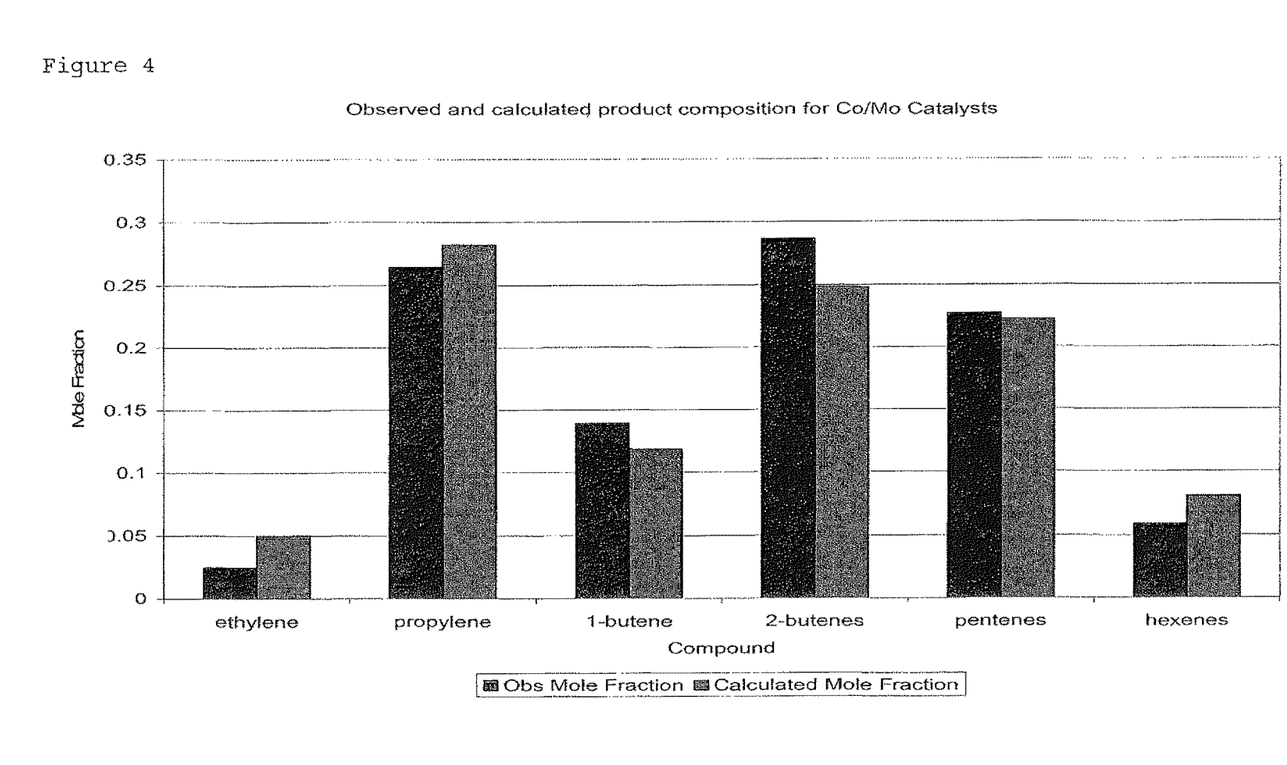
FIG. 4 is a graph comparing the calculated equilibrium and observed product distributions for metathesis of butenes with a cobalt/molybdenum catalyst at 97° C. and 50% 1-butene in feed (Example 3).

The feed with a 1-butene/2-butene molar ratio of 1:1 was passed continuously through the catalyst bed of CoO/MoO$_3$ on alumina (3.5 wt % CoO, 14 wt % MoO$_3$) which was maintained at 97° C. The catalyst was previously activated in nitrogen at 500° C. Reaction product analysis after 9 hours time on stream revealed a total butenes conversion of 57% with an equilibrium distribution of products. The selectivity towards propylene was found to be 46% while the selectivity towards hexenes was approximately 10%. A comparison between the calculated equilibrium product distribution and the observed values is shown in FIG. 4.

Example 4: WO$_3$ Catalyst at 296° C., 50% 1-Butene

Figure 5:
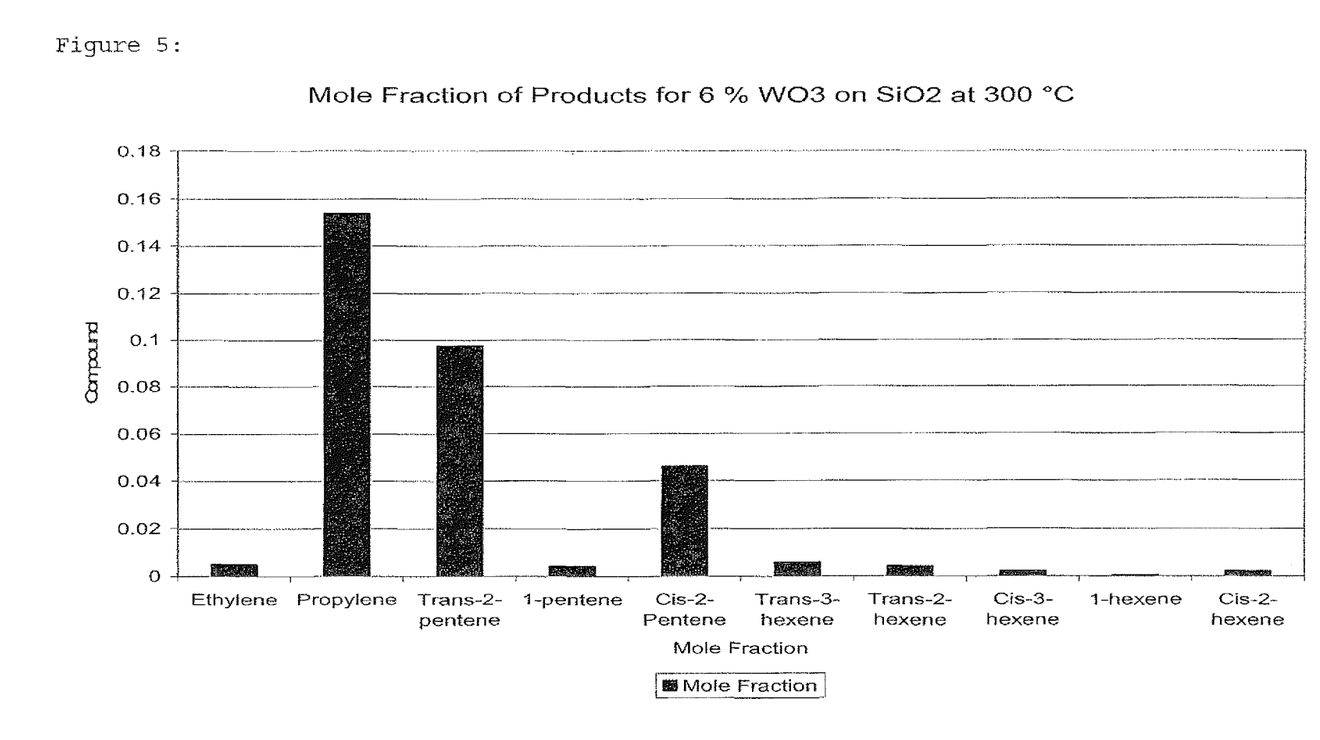
FIG. 5 is a graph of the observed product distribution for metathesis of butenes with a 6% tungsten oxide catalyst at 296° C. and 50% 1-butene in feed (Example 4).

The feed with a 1-butene/2-butene molar ratio of 3:1 was passed continuously through the catalyst bed of WO$_3$ on silica (6 wt % WO$_3$) which was maintained at 296° C. The catalyst was previously activated in nitrogen at 600° C. Reaction product analysis after 45 minutes time on stream revealed a total butenes conversion of 42% with an equilibrium distribution of products. The selectivity towards propylene was found to be 48% while the selectivity towards hexenes was 5%. The experimental product distribution is shown in FIG. 5.

Aromatization

Catalyst:

The catalyst was Pt/CsGeZSM-5 made by the methods disclosed in U.S. Patent Application Publication no. 2008/0255398.

EXAMPLES

A mixture of 14% cis-3-hexene and 86% trans-3-hexene was blended with n-hexane at varying levels and used as reactor feed. This 1:6 ratio of cis:trans is close to the calculated equilibrium ratio of 12% cis and 88% trans at this temperature. Different levels of hexene were used since the product from the metathesis process may possibly be blended with other C$_6$ feeds. The testing conditions below were used. GC data for the individual compounds show that much of the 3-hexene is quickly hydrogenated to n-hexane, some of which is dehydrogenated again to 1- and 2-hexenes. The procedure was repeated for 1-hexene. The results are shown in Table 1 below.

TABLE 1

1% Pt/CsGeZSM-5 catalyst. Conversion and aromatics selectivity measured at T = 515° C., P = 1 atm, H$_2$/HC in feed = 0.75, LHSV = 8.6 hr$^{-1}$.

| Feed composition (wt. %) | | | | |
|---|---|---|---|---|
| n-hexane | 3-hexenes | 1-hexene | C$_6$ conversion | aromatics selectivity |
| 100 | 0 | 0 | 18 | 91 |
| 90 | 10 | 0 | 17 | 91 |
| 70 | 30 | 0 | 20 | 89 |
| 0 | 100 | 0 | 30 | 86 |
| 90 | 0 | 10 | 23 | 89 |
| 70 | 0 | 30 | 25 | 89 |
| 0 | 0 | 100 | 30 | 89 |

From these data we can see that both 1-hexene and the 3-hexenes are converted to benzene with good selectivity and the rate of conversion of both is somewhat higher than that of n-hexane. Selectivity to aromatics (which were predominantly benzene) declines slightly as the level of olefin increases, probably because the olefin cracks somewhat faster than the paraffin. The rate of deactivation was unaffected by olefin concentrations up to 30%.

Figure 1:
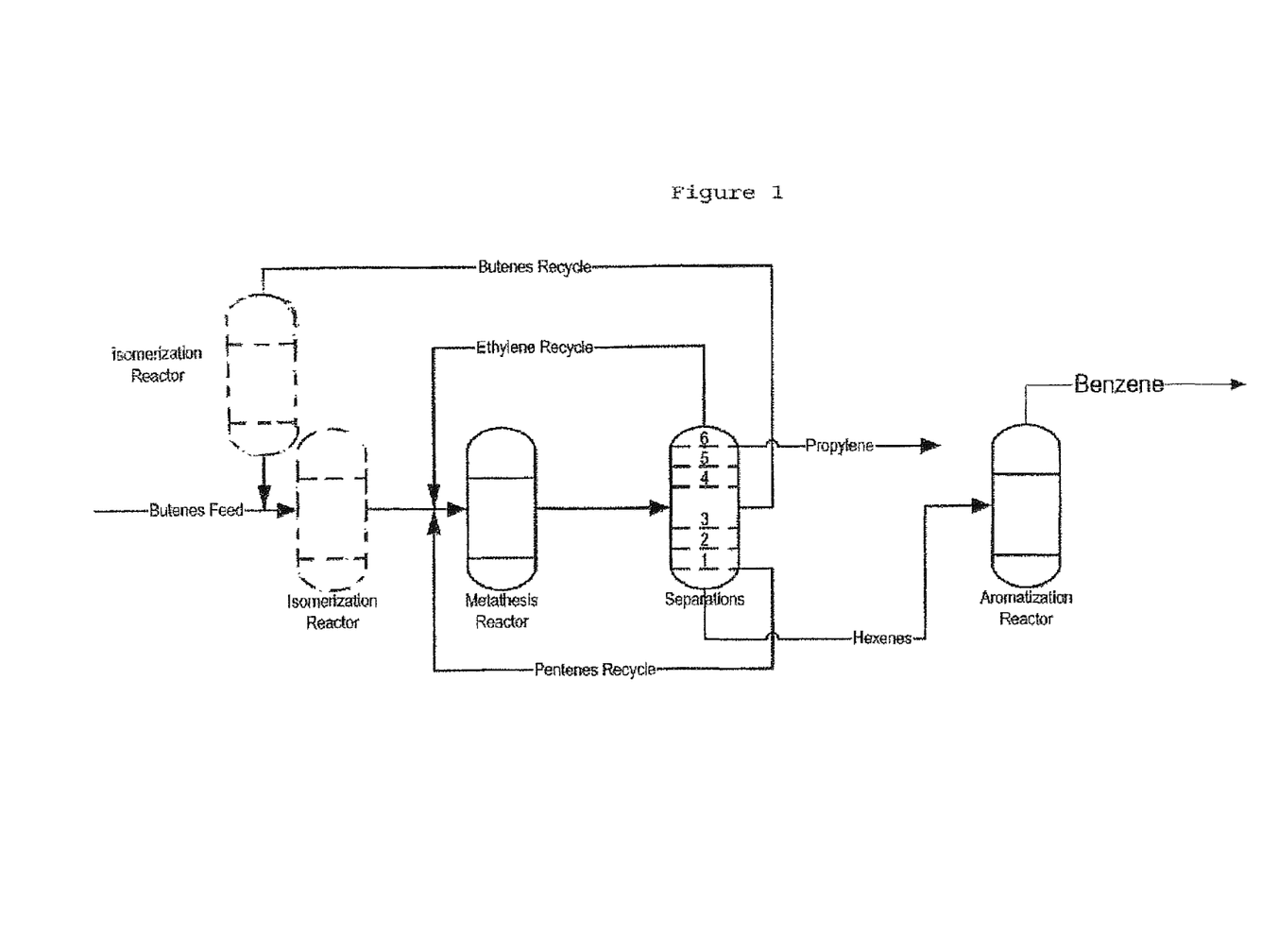
FIG. 1 is a diagram of a multistage process for metathesis of butenes to propylene and hexene and aromatization of hexene to benzene.

FIG. 1 shows an embodiment of the present disclosure. A hydrocarbon feed containing butenes (1-butene, 2-butene and, optionally, isobutene) is introduced into the process. The feed may also contain pentenes. The feed may be combined with a recycle stream containing product butenes. Depending on feed composition before combination with the recycle and on composition of the recycle stream, either the recycle stream or the feed after combination with the recycle may be modified in an isomerization reactor to obtain a desired molar ratio of 1-butene:2-butene for the feed composition into the metathesis reactor, i.e., the isomerization reactor may be located in the recycle stream or in the feed stream after combination with the recycle. Before being introduced into the metathesis reactor the feedstream may be combined with recycle streams containing pentenes and ethylene. The feed introduced into the metathesis reactor may contain butenes (1-, 2- and iso), pentenes and ethylene. Some possible metathesis reactions are disclosed above. As noted above, any metathesis catalyst should be effective for the present disclosure. The desired products of the metathesis reaction are propylene and hexene. Pentenes, product butenes and ethylene are byproducts which may be recycled (along with unreacted butenes). Ethylene may be separated for further processing into other compound and products instead of being recycled. In addition to the products for recycle, the reaction products from the metathesis reactor are separated into at least two product streams, one containing propylene and one containing hexenes and higher olefins, and recycle stream(s) of unreacted butenes and pentenes. As noted above, ethylene may be recycled or product. Any separation technique known in the art to yield these products and recycle may be used in the present disclosure. After separation, the hexene product stream is introduced into an aromatization reactor for conversion to aromatics. The hexenes are converted to benzene. The higher olefins, such as heptenes and octenes, are converted to toluene, xylenes, ethylbenzene and styrene. Any aromatization catalyst known in the art for aromatizing olefins may be used in the present disclosure.

Obviously, numerous modifications and variations of the present disclosure are possible in light of the above teachings. It is therefore to be understood that within the scope of the appended claims, the disclosure may be practiced otherwise than as specifically described herein.

What is claimed is:

1. A process for producing propylene and aromatics comprising:
   a) reacting in a metathesis reactor a hydrocarbon feed mixture comprising 1-butene, 2-butene and, optionally, isobutene in the presence of a metathesis catalyst at conditions to produce a product comprising ethylene, propylene, product butenes, pentenes, hexenes and higher olefins;
   b1) separating from the product and recycling to the metathesis reactor the pentenes, the butenes, and optionally, the ethylene;
   b2) separating the propylene from the product;
   b3) separating the hexenes and higher olefins from the product; and
   c) reacting the hexenes and higher olefins to aromatics in the presence of an aromatization catalyst,
   wherein in step a) the molar ratio of 1-butene:2-butene in the hydrocarbon feed is in the range of from about 1:6 to about 6:1.

2. The process of claim 1, wherein the metathesis catalyst is $WO_3$ on $SiO_2$, $MoO_3$ on $Al_2O_3$ or $Re_2O_7$ on $Al_2O_3$.

3. The process of claim 1, wherein the concentration of hexenes and higher olefins is up to 30%.

4. The process of claim 1, wherein the hydrocarbon feed mixture additionally comprises pentenes.

5. The process of claim 1, wherein the molar ratio of 1-butene:2-butene in the hydrocarbon feed is about 2:1.

6. The process of claim 1, wherein the hydrocarbon feed comprises a level of non-diene impurities, contaminants and poisons of no more than 100 ppm.

7. The process of claim 6, wherein the impurities, contaminants and poisons are acetylenic compounds, polar molecules, oxygenates, sulfur compounds, nitrogen compounds or combinations thereof.

8. The process of claim 7, wherein the polar molecule is water.

9. The process of claim 1, wherein metathesis is carried out at a temperature in the range of from about 25° C. to about 400° C. and a pressure in the range of from about 0 psig to about 500 psig.

10. The process of claim 1, wherein aromatization is carried out at a liquid hourly space velocity in the range between 0.1 and 100 $h^{-1}$, at a temperature in the range between 200 and 600° C. and at a pressure in the range between 1 and 315 psia.

11. The process of claim 1, wherein, after the butenes are recycled to the hydrocarbon feed, the hydrocarbon feed is isomerized to a 1-butene:2-butene molar ratio in the range of from about 1:6 to about 6:1 prior to being introduced into the metathesis reactor.

12. The process of claim 1, wherein the butenes are isomerized prior to being recycled to the hydrocarbon feed and the hydrocarbon feed has a 1-butene:2-butene molar ratio in the range of from about 1:6 to about 6:1 prior to being introduced into the metathesis reactor.

13. The process of claim 1, wherein the propylene: hexenes molar ratio in step a) is about 2:1.

14. The process of claim 1, wherein the propylene: hexenes molar ratio in the product is in the range of from about 1:1 to about 3:1.

15. The process of claim 1, wherein the concentration of hexenes in the product is about three to about twenty mole %.

16. A process for producing propylene and aromatics comprising:
   a) reacting in a metathesis reactor a hydrocarbon feed mixture comprising 1-butene, 2-butene and, optionally, isobutene in the presence of a metathesis catalyst at conditions to produce a product comprising ethylene, propylene, product butenes, pentenes, hexenes and higher olefins;
   b1) separating from the product and recycling to the metathesis reactor the pentenes, the butenes, and optionally, the ethylene;
   b2) separating the propylene from the product;
   b3) separating the hexenes and higher olefins from the product; and
   c) reacting the hexenes and higher olefins to aromatics in the presence of an aromatization catalyst, wherein greater than or equal to 86% aromatic selectivity is achieved;
   wherein in step a) the molar ratio of 1-butene:2-butene in the hydrocarbon feed is in the range of from about 1:6 to about 6:1.

17. A process for producing propylene and aromatics comprising:
   a) reacting in a metathesis reactor a hydrocarbon feed mixture comprising 1-butene, 2-butene and, optionally, isobutene in the presence of a metathesis catalyst at conditions to produce a product comprising ethylene, propylene, product butenes, pentenes, hexenes and higher olefins;

b1) separating from the product and recycling to the metathesis reactor the pentenes, the butenes, and optionally, the ethylene;
b2) separating the propylene from the product;
b3) separating the hexenes and higher olefins from the product; and
c) reacting 3-hexene and higher olefins to aromatics in the presence of an aromatization catalyst, wherein in step a) the molar ratio of 1-butene:2-butene in the hydrocarbon feed is in the range of from about 1:6 to about 6:1.

\* \* \* \* \*